United States Patent [19]
Sprecker et al.

[11] Patent Number: 4,780,564
[45] Date of Patent: Oct. 25, 1988

[54] ALLYL 4-CYCLOOCTENYL GLYCOLATE, ORGANOLEPTIC USES THEREOF, PROCESS FOR PREPARING SAME AND INTERMEDIATES USEFUL IN SAID PROCESS

[75] Inventors: Mark A. Sprecker, Sea Bright; William L. Schreiber, Jackson; Robert P. Belko, Woodbridge, all of N.J.

[73] Assignee: International Flavors & Fragrances Inc., New York, N.Y.

[21] Appl. No.: 66,965

[22] Filed: Jun. 29, 1987

[51] Int. Cl.⁴ .................... C07C 69/734; C07C 59/62
[52] U.S. Cl. .................................... 560/126; 252/8.9; 252/174.11; 562/508; 512/4; 512/8; 424/69; 424/70; 424/76.4
[58] Field of Search ....................... 560/126; 562/508; 512/4, 8

[56] References Cited

U.S. PATENT DOCUMENTS

| | | | |
|---|---|---|---|
| 2,882,292 | 4/1959 | Schlechting et al. | 562/508 |
| 3,468,929 | 9/1969 | Bonnet | 560/126 |
| 4,052,435 | 10/1977 | Wilke et al. | 560/126 |
| 4,152,456 | 5/1979 | Bagli et al. | 562/508 |

*Primary Examiner*—Vivian Garner
*Attorney, Agent, or Firm*—Arthur L. Liberman

[57] ABSTRACT

Described is allyl 4-cyclooctenyl glycolate of our invention having the structure:

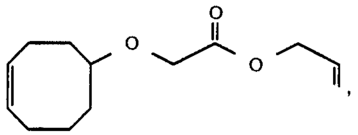

and the perfumery use thereof in augmenting or enhancing the aroma of perfume compositions, colognes and perfumed articles including solid or liquid anionic, cationic, nonionic or zwitterionic detergents, fabric softener compositions, fabric softener articles, hair preparations and cosmetic powders. The genus defined according to the structure:

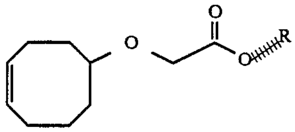

wherein R represents hydrogen, allyl or alkali metal and:

represents a covalent bond wherein R represents hydrogen or allyl and an ionic bond where R represents alkali metal defines all of the products of our invention including intermediates useful in the process for preparing the compound having the structure:

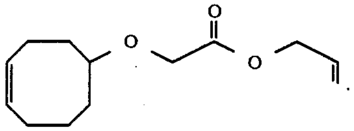

2 Claims, 3 Drawing Sheets

GLC PROFILE FOR EXAMPLE I.
CRUDE

NMR SPECTRUM FOR EXAMPLE I.

ALLYL 4-CYCLOOCTENYL GLYCOLATE, ORGANOLEPTIC USES THEREOF, PROCESS FOR PREPARING SAME AND INTERMEDIATES USEFUL IN SAID PROCESS

BACKGROUND OF THE INVENTION

This invention relates to compounds defined according to the genus:

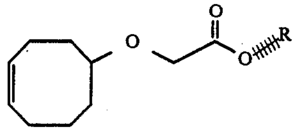

wherein R represents hydrogen, allyl or alkali metal and:

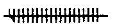

represents a covalent bond when R represents hydrogen or allyl and an ionic bond when R represents alkali metal.

Inexpensive chemical compounds which can provide natural, pineapple and chamomile aroma nuances are highly desirable in the art of perfumery. Many of the naturl materials which provide such fragrances and contribute such desired nuances to perfumery compositions are high in cost, unobtainable at times, vary in quality from one batch to another and/or are generally subject to the usual variations of natural products.

There is, accordingly, a continuing effort to find synthetic materials which will provide, enhance or augment the fragrance notes provided by natural essential oils or compositions thereof. Unfortunately, many of the synthetic materials either have the desired nuances only to a relatively small degree or they contribute undesirable or unwanted odor to perfume compositions, perfumed articles and colognes.

Allyl alkyl glycolates are known for use in the art of perfumery. However, these compounds do not contribute fruity (pineapple) and/or chamomile aroma nuances to perfume compositions, colognes or perfumed articles as does the allyl 4-cyclooctenyl glycolate of our invention.

Indeed, the allyl 4-cyclooctenyl glycolate of our invention has unexpected, unobvious and advantageous aroma properties when compared to other allyl glycolates of the prior art.

Thus, moderately "weak" galbanum type materials are being marketed including the compound having the structure:

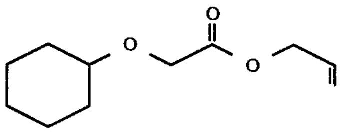

which is marketed as "CYCLOGALBANATE" by Dragoco S. A. of West Germany. Allyl amyl glycolate having the structure:

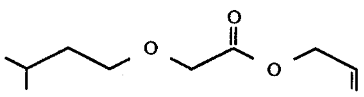

is marketed by International Flavors & Fragrances Inc..

Nothing in the prior art however discloses the unobvious and advantageous aroma properties (e.g., strength and substantivity) of the compound having the structure:

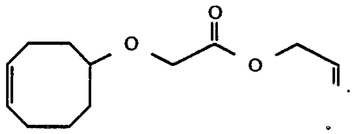

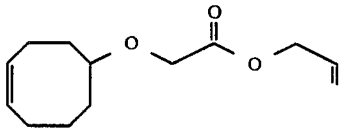

(Conditions: SE-30 column programmed at 180° C. isothermal).

Figure 2:
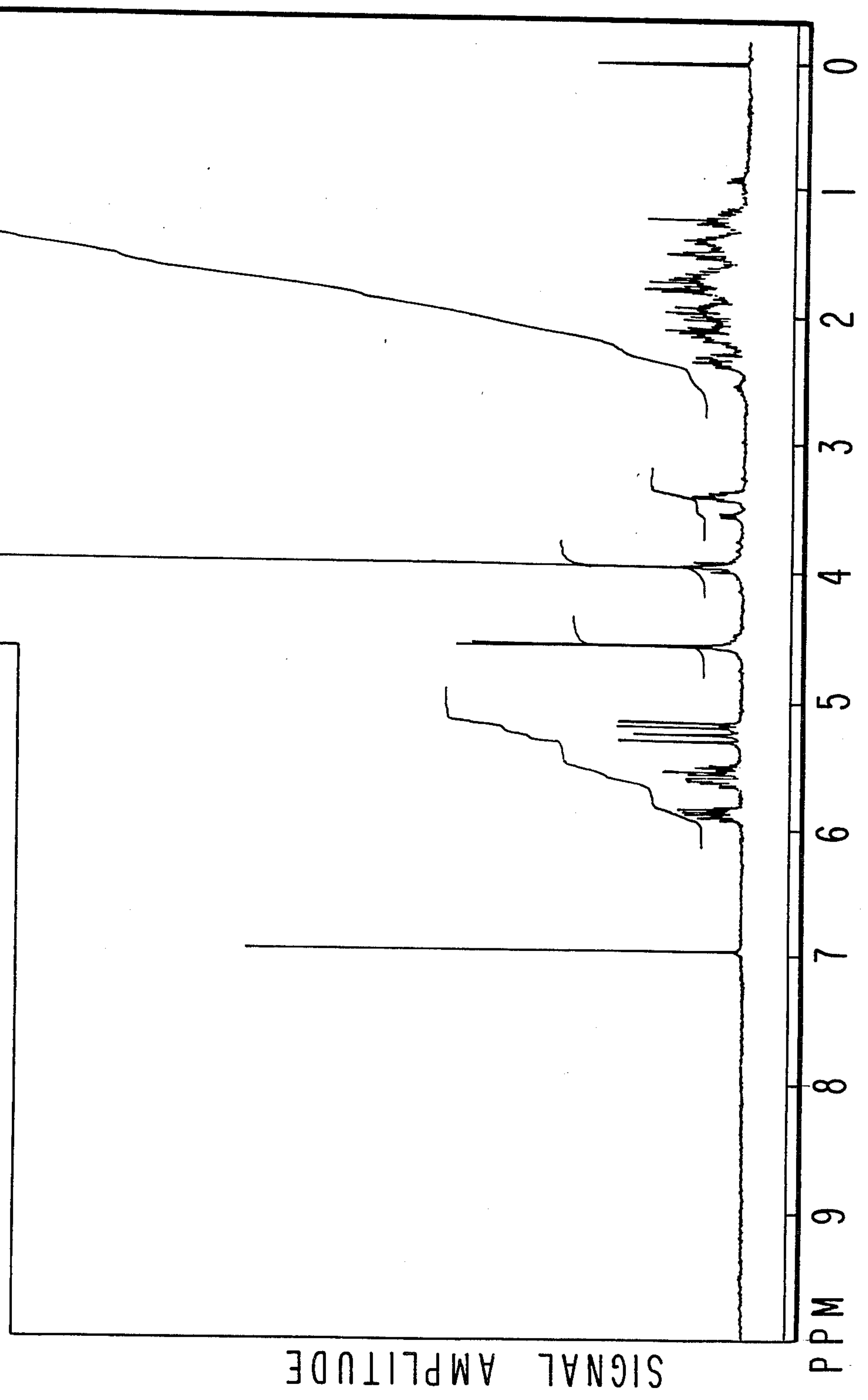

FIG. 2 is the NMR spectrum for the compound having the structure:

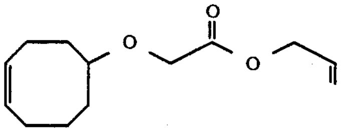

produced according to Example I.

Figure 3:
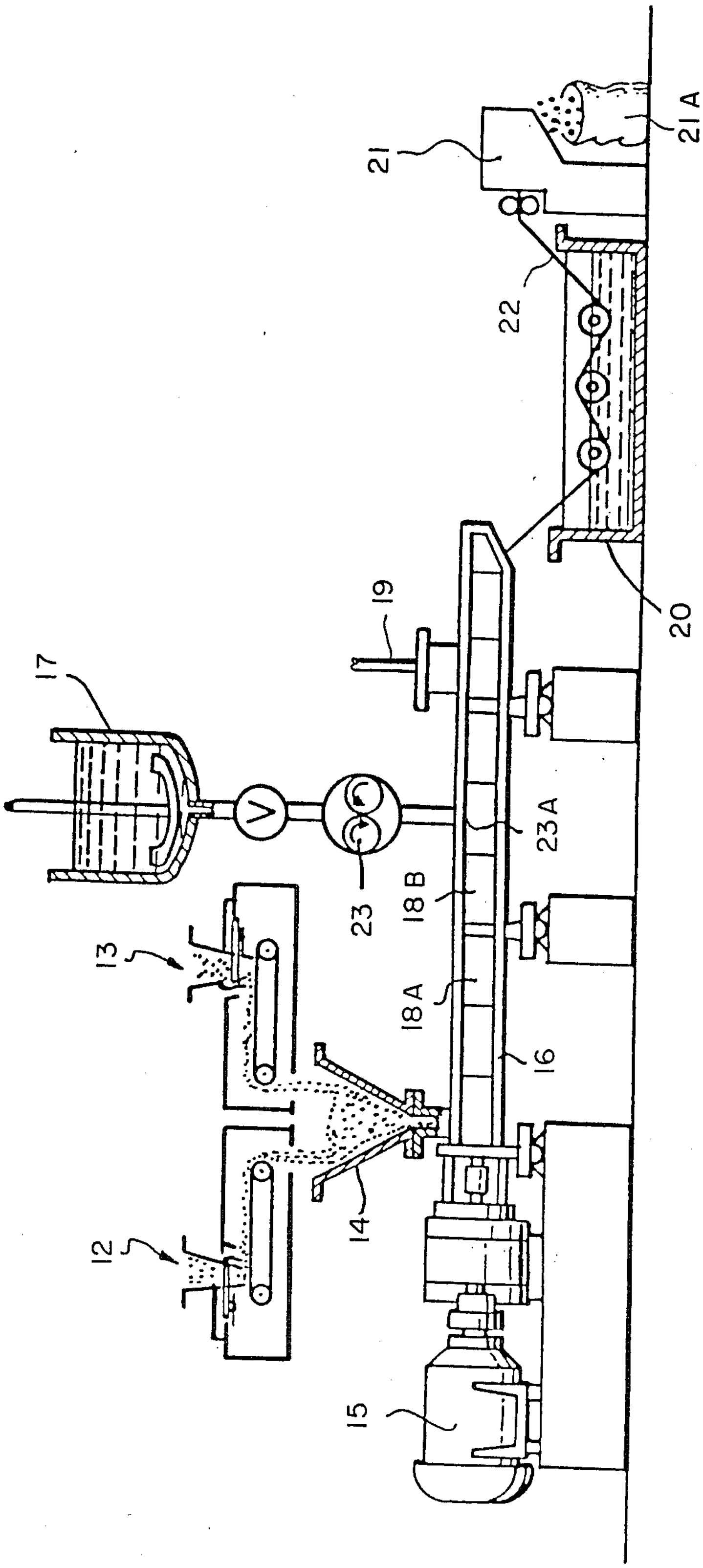

FIG. 3 is a cut-away side elevation schematic diagram of a screw extruder during the compounding of a resin with a perfume composition at least containing the compound having the structure:

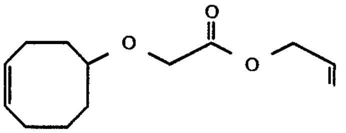

while simultaneously adding foaming agent into the hollow portion of the barrel of the extruder and incorporates pelletizing apparatus used in pelletizing extruded foamed tow produced as a result of the extrusion operation.

DETAILED DESCRIPTION OF THE DRAWINGS

FIG. 3 is a schematic cut-away elevation diagram of extrusion and pelletizing apparatus useful in carrying out a process of our invention during the operation of said apparatus whereby perfuming material containing the compound having the structure:

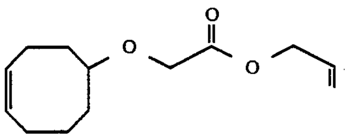

is incorporated into a resin. Motor 15 drives the extruder screws located at 23A in barrel 16, the extruder being operated at temperatures in the range of about 150 up to about 250° C. At the beginning of the barrel resin at source 12 together with additives, e.g., opacifiers, processing aids, colors, pearlescent agents and densifiers at location 13 is added via addition funnel 14 into the extruder. Simultaneously (when the operation reaches "steady state"), a perfumant containing the compound having the structure:

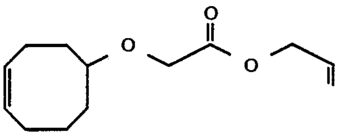

is added to the extruder at one, two or more of barrel segments 3-8 of the extruder (which may be a twin screw or single screw extruder) at locations **18*a*, 18*b*, 18*c* and 18*d* by means of gear pump 23 from source 17. From source 19 into barrel segments 5-10**, gaseous or liquid blowing agents, e.g., nitrogen, carbon dioxide and the like is described, supra, are added simultaneously with the addition of the perfumant containing the compound having the structure:

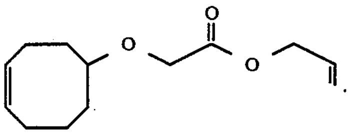

The feed rate range of resin is about 80-300 pounds per hour. The feed rate range of the perfumant is between 1 and 35% of the feed rate range of the resin. The blowing agent rate range is such that the pressure of the gas or the pressure over the perfumant being fed into the extruder is between about 50 and 200 psig. If desired, the extruded ribbon or cylinder may be passed through water bath 20 and pelletizer 21 into collection apparatus 21A.

THE INVENTION

The present invention provides the compound, the allyl 4-cyclooctenyl glycolate having the structure:

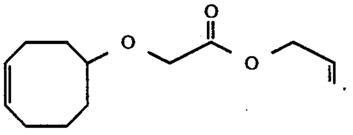

The present invention also provides uses of said allyl 4-cyclooctenyl glycolate in augmenting or enhancing the aroma of perfume compositions, colognes and perfumed articles (e.g., solid or liquid anionic, cationic, nonionic or zwitterionic detergents, fabric softener compositions, fabric softener articles, perfumed polymers and cosmetic powders).

Also described is a process for preparing the allyl 4-cyclooctenyl glycolate having the structure:

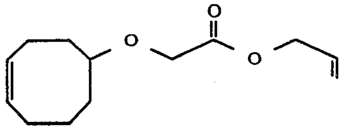

using, interalia, as a starting material 4-cyclooctenol having the structure:

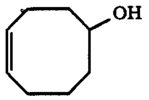

as well as a haloacetic acid salt having the structure:

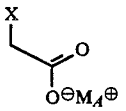

wherein X represents chloro, bromo or iodo and $M_A$ represents alkali metal, e.g., sodium potassium or lithium.

Thus, 4-cyclooctenol having the structure:

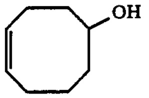

is reacted with an alkali metal hydride having the structure:

$M_B$—H according to the reaction:

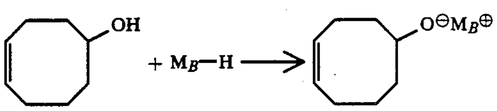

whereby the alkali metal salt of 4-cyclooctenol is produced having the structure:

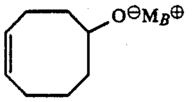

where $M_B$ represents alkali metal. The resulting alkali metal salt of 4-cyclooctenol is then reacted with an alkali metal salt of a halo acetic acid having the structure:

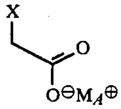

to yield an alkali metal salt of 4-cyclooctenyloxyacetic acid according to the reaction:

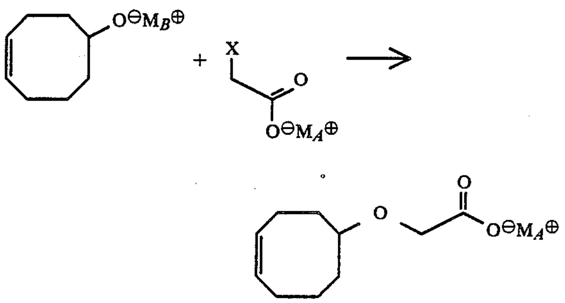

wherein X represents chloro, bromo or iodo; wherein $M_A$ and $M_B$ represent the same or different alkali metal.

The resulting alkali metal salt of the 4-cyclooctenyloxyacetic acid having the structure:

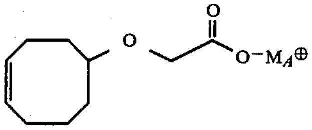

is then acidified and then reacted with allyl alcohol under esterification conditions to yield the allyl ester of 4-cyclooctenyloxyacetic acid having the structure:

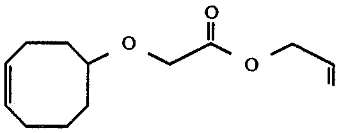

according to the reactions:

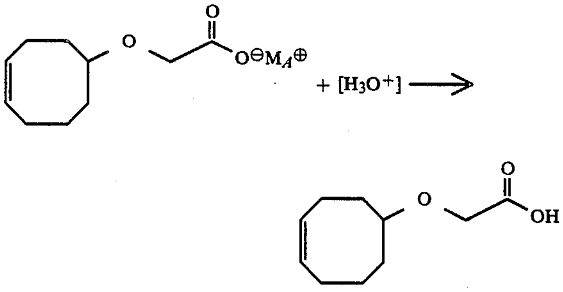

and

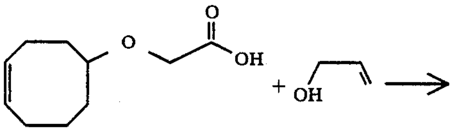

-continued

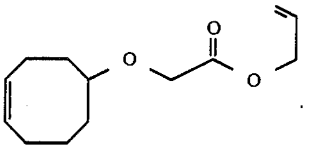

The alkali metal that may be used and is represented by $M_A$ or $M_B$ may be sodium, potassium or lithium. The moiety X is a halogen which may be either of chloro, bromo or iodo.

The reactant having the structure:

$M_B$—H is most preferably sodium hydride whereby the reaction:

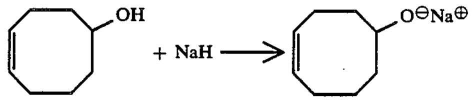

is the preferable reaction in order to form the salt:

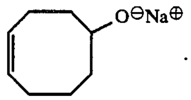

The most preferable alkali metal salt of a halo acetic acid is the compound having the structure:

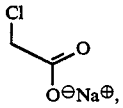

sodium chloro acetate which would enable the most preferred reaction to take place:

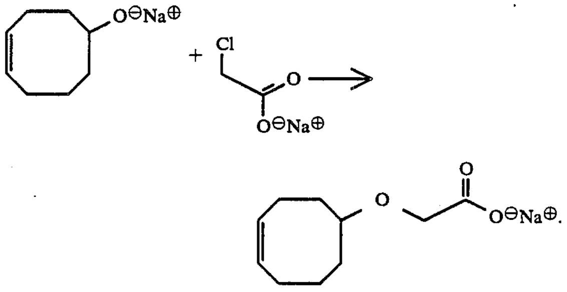

The resulting preferred salt having the structure:

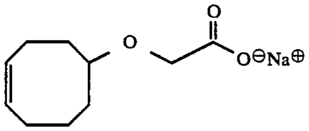

is then acidified using an acid such as hydrochloric acid to form the free acid, 4-cyclooctenyloxyacetic acid according to the reaction:

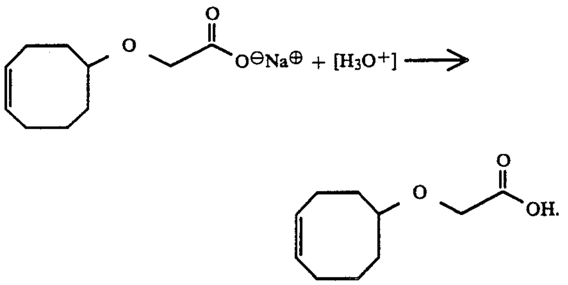

This acid is then esterified with allyl alcohol in the presence of an esterification reagent such as concentrated sulfuric acid according to the reaction:

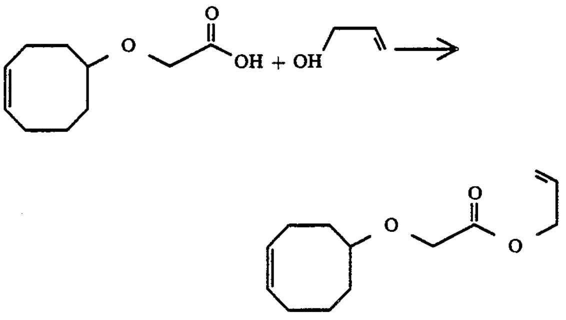

whereby the compound having the structure:

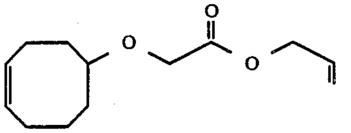

is formed.

The resulting product is preferably fractionally distilled in order to yield an organoleptically efficacious ester, the allyl ester of 2-(4-cyclooctenyl)oxyacetic acid having the structure:

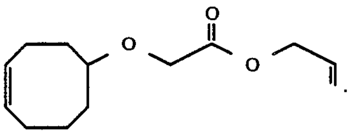

The reaction of the 4-cyclooctenyl alcohol with the alkali metal hydride, to wit:

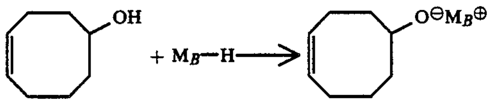

wherein $M_B$ is alkali metal, takes place at a temperature in the range of from about 80° up to about 120° C. preferably in the presence of a solvent which is inert to the reaction product as well as the reactants such as toluene. The reaction time takes place over a period of between one and about five hours at reflux conditions whereby the reaction product, hydrogen is removed from the reaction mass.

The resulting product having the structure:

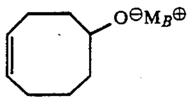

is reacted with an alkali metal salt of a halo acetic acid according to the reaction:

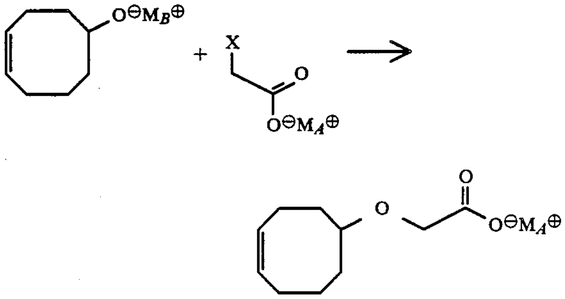

as set forth, supra, wherein $M_A$ and $M_B$ are the same or different alkali metal and wherein X is chloro, bromo or iodo. The reaction takes place at reflux conditions (e.g., about 140° C. at atmospheric pressure) over a period of between about 2 and about 5 hours. The resulting product having the structure:

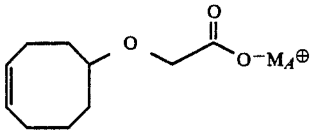

is then acidified prior to being esterified whereby the compound having the structure:

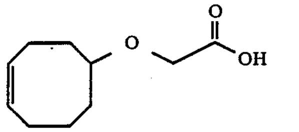

is formed (prior to esterification) according to the reaction:

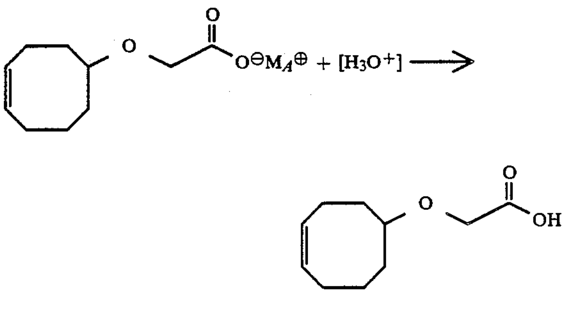

and the resulting acid is then esterified under standard esterification conditions with allyl alcohol to form the ester according to the reaction:

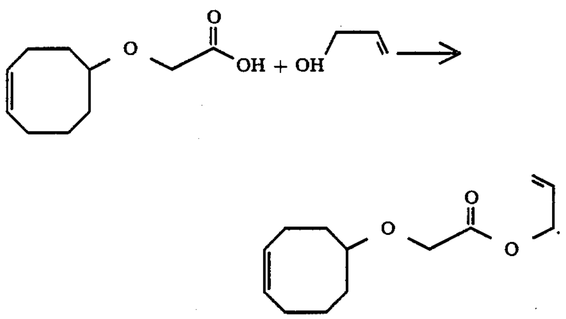

The acidification takes place at ambient conditions using an acid such as hydrochloric acid. The esterification following the acidification takes place at reflux conditions in the presence of a concentrated esterification reagent such as concentrated sulfuric acid or para toluene sulphonic acid with allyl alcohol. The mole ratio of allyl alcohol:acid having the structure:

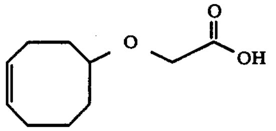

is preferably about 1:1. At the end of the reaction, the resulting product is "worked up" and neutralized with dilute base such as 5% aqueous sodium hydroxide. The resulting product is then distilled as by fractional distillation yielding a product having an intense pineapple and chamomile aroma.

The allyl 4-cyclooctenyl glycolate prepared in accordance with the process of our invention and one or more auxiliary perfume ingredients including, for example, alcohols, aldehydes, terpenic hydrocarbons, ketones, ethers other than the compound having the structure:

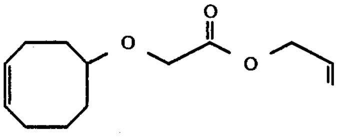

nitriles, esters other than the compound having the structure:

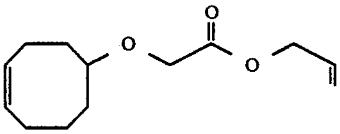
, lactones, natural essential oils, synthetic essential oils, mercaptans and alkyl mercapto derivatives may be admixed so that the combined odors of the individual components produce a pleasant and desired fragrance, particularly and preferably in the floral type fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual compositions which contribute to their particular olfactory, characteristics. However, the over-all sensory effect of the perfume composition will be at least the sum total of the effects of each of the ingredients. Thus, allyl 4-cyclooctenyl glycolate of our invention can be used to alter, modify or enhance the aroma characteristics of a perfume composition, for example, by utilizing or moderating the olfactory reaction contributed by another ingredient in the composition.

The amount of the allyl 4-cyclooctenyl glycolate of our invention which will be effective in perfume compositions as well as in perfumed articles (e.g., solid or liquid detergents, soaps, fabric softener compositions, drier-added fabric softener articles, optical brightener compositions, perfumed polymers and textile sizing agents and colognes) depends on many factors, including the other ingredients, their amounts and the effects which are desired. It has been found that perfume compositions containing as little as 0.01% of the allyl 4-cyclooctenyl glycolate of our invention and less than 50% of the allyl 4-cyclooctenyl glycolate of our invention, or even less (e.g., 0.005%) can be used to impart a pineapple and chamomile aroma to soaps, cosmetics, anionic, nonionic, cationic or zwitterionic detergents, fabric softener compositions, fabric softener articles, optical brightener compositions, textile sizing compositions, perfumed polymers or other products. The amount employed can range up to 70% of the fragrance components and will depend on considerations of cost, nature of the end product, the effect desired on the finished product and the particular fragrance sought.

The allyl 4-cyclooctenyl glycolate of our invention is useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders, and perfumed polymers and articles of manufacture produced from said perfumed polymers. When used as (an) olfactory component of a perfumed article, as little as 0.2% of the allyl 4-cyclooctenyl glycolate of our invention will suffice to impart intense pineapple and chamomile aromas to floral perfume formulations. Generally, no more than 6% of the allyl 4-cyclooctenyl glycolate of our invention based on the ultimate end product is required in the perfumed article composition. Accordingly, the range of the allyl 4-cyclooctenyl glycolate of our invention in the perfumed article is from about 0.2% by weight of the allyl 4-cyclooctenyl glycolate up to about 6% by weight based on the perfumed article. In addition, the perfume composition or fragrance composition of our invention can contain a vehicle or carrier for the allyl 4-cyclooctenyl glycolate of our invention. The vehicle can be a liquid, such as a non-toxic alcohol, e.g., ethyl alcohol, a non-toxic glycol, e.g., propylene glycol or the like. The carrier can also be an absorbent solid, such as a gun (e.g., gum arabic, guar gum or xanthan gum) or components for encapsulating the composition (such as gelatin) as by coacervation; or components for forming polymer wall around a liquid perfumed center such as a urea formaldehyde prepolymer.

Our invention also relates to the utilization of controlled release technology for the controlled release of perfumes into gaseous environments from polymers such as mixtures of epsilon polycaprolactone polymers and polyethylene which poly epsilon caprolactone polymers are defined according to the structure:

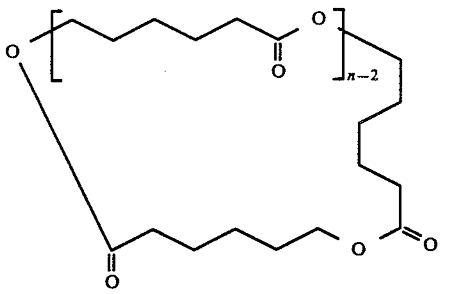

wherein "n" is from about 50 up to about 1,200 with the proviso that the average "n" in the system varies from about 150 up to about 700 according to the mathematical statement:

$$[700 \geqq \bar{\eta} \geqq 150]$$

with the term $\bar{\eta}$ being the average number of repeating monomeric units for the epsilon polycaprolactone polymer. The perfumed material's release rate from such polymer mixture is close to "zero order". As a general rule, the release rate in a polymeric matrix is proportional to $t^{-\frac{1}{2}}$ until about 60% of the functional fluid is released from the polymeric matrix. The release rate thereafter is related exponentially to time as a general rule according to the equation:

$$\frac{dM_1}{dt} = k_1 e^{-k_2 t}$$

wherein $k_1$ and $k_2$ are constants. According to Kydonieus, "Controlled Release Technologies: Methods, Theory, and Applications" (cited, supra), the amount of perfume composition released is proportional to time as long as the concentration of perfume material present, e.g., the allyl 4-cyclooctenyl glycolate of our invention is higher than the solubility of the agent in the matrix. Thus, such dispersed systems are similar to the dissolved systems except that instead of a decreased release rate after 60% of the perfume material has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-dependent phenomenon, the release being constant (zero order) as long as the surface area does not change during the erosion process. This is the case with the polymers containing the allyl 4-cyclooctenyl glycolate of our invention.

The polyepsilon carpolactone polymers useful in practicing our invention are more specifically described in the brochure of the Union Carbide Corporation, 270 Part Avenue, New York, N.Y. 10017, entitled "NEW POLYCAPROLACTONE THERMOPLASTIC POLYMERS PL-300 AND PCL-700". These polyepsilon caprolactone polymers are composed of a repeating sequence of non-polar methylene groups and relatively polar ester groups. The average number of repeating monomeric units varies between 150 and 700 depending on the particular "PCL" number. Thus, regarding PCL-300 the average number of repeating monomeric units is about 300. Regarding PCL-700, the average number of repeating monomeric units is 700.

The polyepsilon caprolactone homopolymers which are ultimately taken in admixture with such materials as polyethylene useful in the practice of our invention may also be stabilized using stabilizers as defined in U.S. Pat. No. 4,360,682 issued on Nov. 23, 1982, the specification for which is incorporated herein by reference. The stabilizing materials which stabilize the polyepsilon caprolactone useful in conjunction with our invention against discoloration are dihydroxybenzenes such hydroquinone or compounds having the formula:

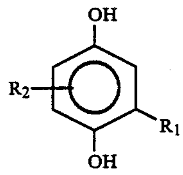

OR

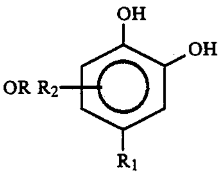

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfere with the functional fluids dissolved and/or adsorbed into the polymeric matrix.

The method for incorporating the allyl 4-cyclooctenyl glycolate of our invention or perfume compositions containing same into polymers may be according to the technique of U.S. Pat. No. 3,505,432 issued on Apr. 7, 1970 (the specification for which is incorporated by reference herein) or U.S. Pat. No. 4,247,498 issued on Jan. 27, 1981, the disclosure of which is incorporated by reference herein.

Thus, for example, a first amount of liquid polyethylenepolyepsilon caprolactone polymer mixture (50:50) is mixed with the allyl 4-cyclooctenyl glycolate of our invention. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained is solidified subsequent to or prior to ultimate casting into a utilitarian shape.

Thus, in accordance with one aspect of our invention the imparting of a scent is effected in two stages. In a first stage, a 50:50 (weight:weight) polyepsilon caprolactone, e.g., PCL-700:polyethylene in molten form is admixed with a high percentage of the allyl 4-cyclooctenyl glycolate of our invention and the mixture is solidified in the form of pellets or beads. These pellets or beads thus contain a high percentage of allyl 4cyclooctenyl glycolate of our invention (e.g., up to 45% by weight of the entire mixture) and may be used as "master pellets" which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification No. 1,589,201 published on May 7, 1981, the specification for which is incorporated by reference therein.

In accordance with the present invention the allyl 4-cyclooctenyl glycolate of our invention is added to the polymer in a lage closed container or drum which is maintained under controlled temperature conditions while the polymer in a melted condition is mixed with the allyl 4-cyclooctenyl glycolate of our invention under agitation.

The following Example I serves to illustrate a process for preparing the allyl 4-cyclooctenyl glycolate of our invention having the structure:

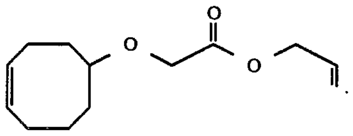

The examples following Example I are illustrative of the organoleptic utilities of the allyl 4-cyclooctenyl glycolate of our invention. All parts and percentages given herein are by weight unless otherwise specified.

EXAMPLE I

Preparation of Allyl 4-Cyclooctenyl Glycolate

Reactions:

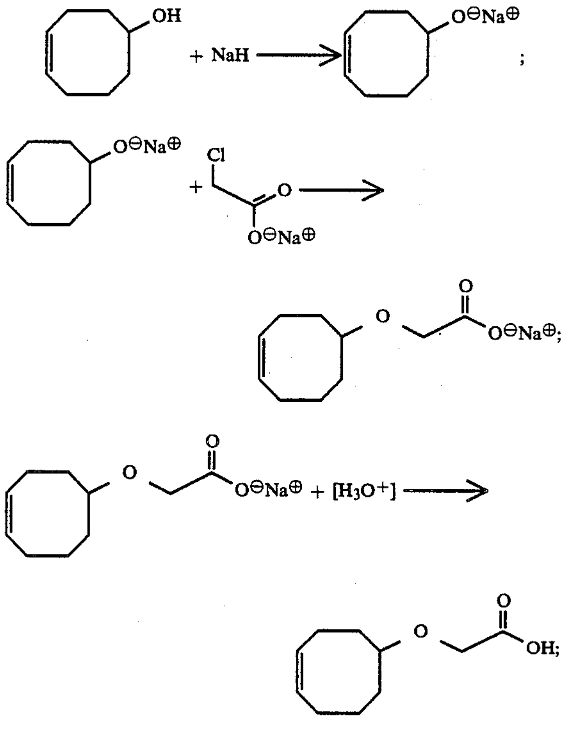

and

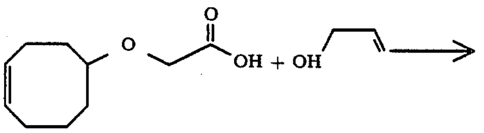

-continued

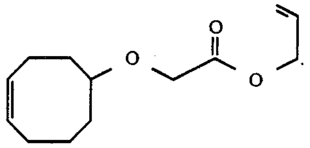

Into a 2 liter reaction vessel equipped with stirrer, thermometer, reflux condenser and heating mantle are placed 877 grams of 4-cyclooctenol and 80 grams of sodium hydride. The resulting mixture is heated at 100° C. with stirring for a period of one hour.

The resulting mixture is then heated to 140° C. and over a period of 0.5 hours, 232 grams of 2-chloroacetic acid is added to the reaction mass. The reaction mass is heated at 140° C. with stirring for a period of three hours.

At the end of the three hour period, the reaction mass is poured into water and acidified with hydrochloric acid (5%). The resulting crude reaction product is intimately admixed with 250 grams of allyl alcohol, 100 grams of toluene and 5 grams of sulfuric acid. The resulting mixture is added to a 1 liter flask equipped with heating mantle, reflux condenser, thermometer and Bidwell trap in order to remove water of reaction.

The resulting reaction mass is then heated to reflux for a period of three hours while removing water of reaction in the Bidwell trap.

The reaction mass is cooled to room temperature and 2 liters of water are added. The organic phase is separated from the aqueous phase and the organic phase is washed with 1 liter of a 5% aqueous sodium hydroxide solution.

The reaction mass is fractionally distilled yielding the compound having the structure:

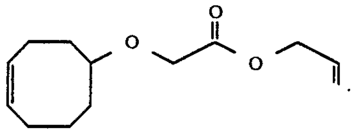

The compound having the structure:

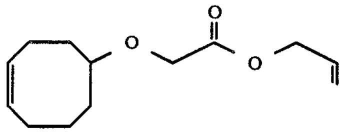

has an intense pineapple and chamomile aroma profile.

Figure 1:
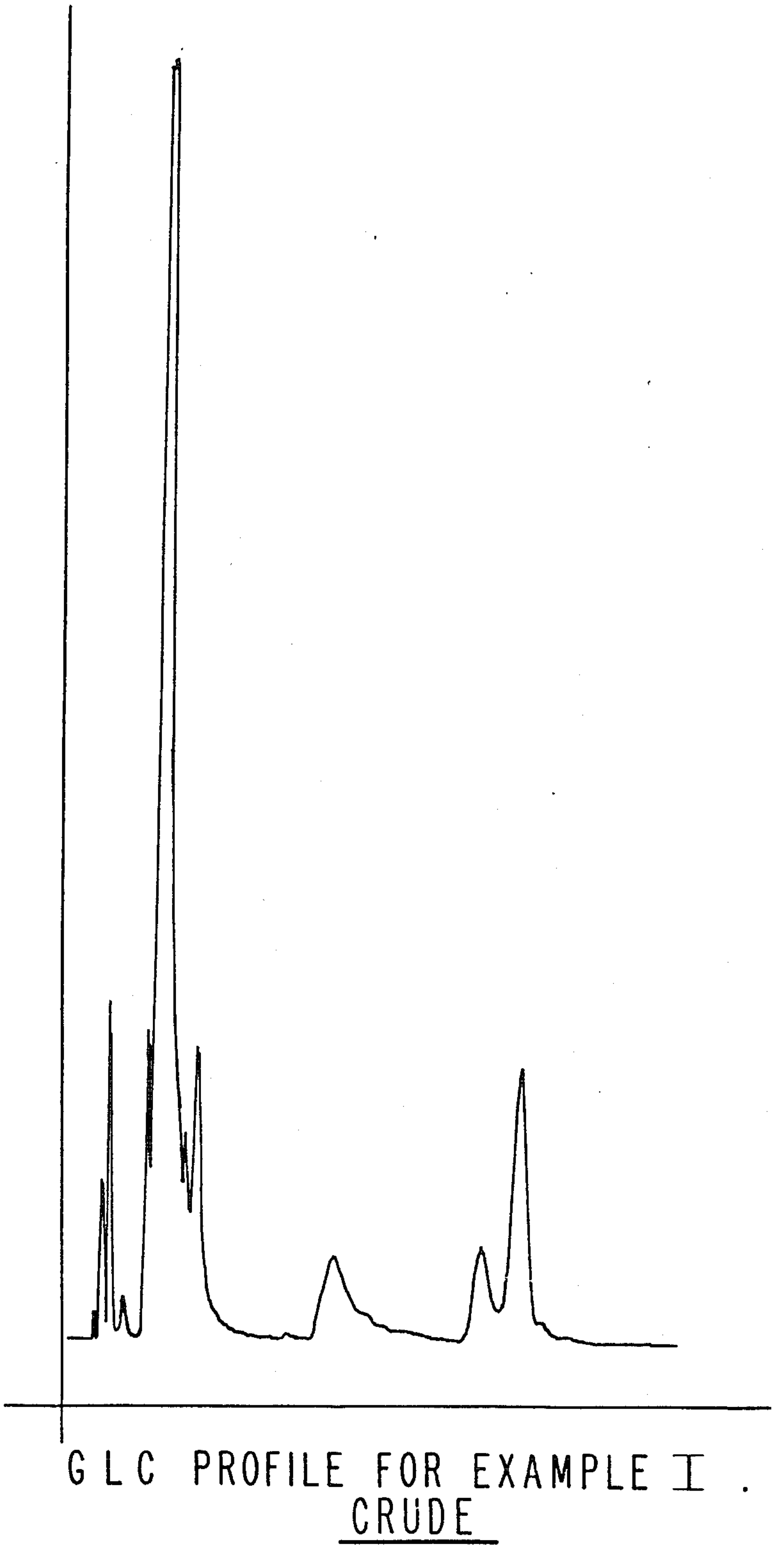
FIG. 1 is the GLC profile for the crude reaction product of Example I containing the compound having the structure.

FIG. 1 is the GLC profile for the crude reaction product containing the compound having the structure:

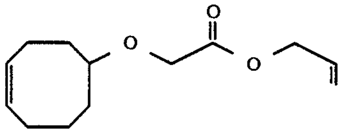

(Conditions: SE-30 column programmed at 180° C. isothermal)

FIG. 2 is the NMR spectrum for the compound having the structure:

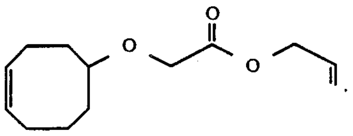

EXAMPLE II

Chamomile Formulation

The following chamomile formulation is prepared:

| Ingredients | Parts by Weight |
|---|---|
| Compound having the structure: 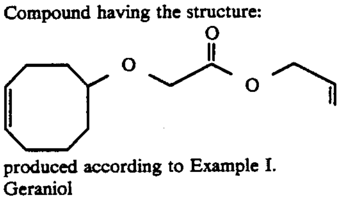 produced according to Example I. | 24.0 |
| Geraniol | 04.0 |
| Citronellol | 04.0 |
| Oil of Chamomile | 12.0 |

The resulting product is an excellent chamomile formulation containing pineapple undertones. Thus, the resulting formulation can be described as "natural chamomile with intense pineapple undertones".

EXAMPLE III

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| Substance | Aroma Description |
|---|---|
| Compound having the structure: 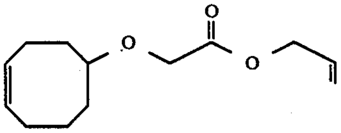 prepared according to Example I. | A pineapple and chamomile aroma profile. |
| Perfume formulation of Example II. | Natural chamomile with intense pineapple undertones. |

EXAMPLE IV

Perfumed Liquid Detergents

Concentrated liquid detergents (lysine salt of n-dodecylbenzene sulfonic acid as more specifically described in U.S. Pat. No. 3,948,818 issued on Apr. 6, 1976 incorporated by reference herein) with aroma nuances as set forth in Table I of Example III, supra are prepared containing 0.10%, 0.15%, 0.20%, 0.25% 0.30% and 0.35% of the substance as set forth in Table I of Example III, supra. They are prepared by adding and homogeneously mixing the appropriate quantity of substance set forth in Table I of Example III, supra in the liquid detergent. The detergents all possess excellent aromas as set forth in Table I of Example III, supra, the intensity increasing with greater concentrations of substance as set forth in Table I of Example III, supra.

EXAMPLE V

Preparation of Colognes and Handkerchief Perfumes

Compositions as set forth in Table I of Example III, supra, are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example III, supra, are imparted to the colognes and to the handkerchief perfumes at all levels indicated.

EXAMPLE VI

Preparation of Soap Compositions

One hundred grams of soap chips (per sample) (IVORY ®, produced by the Procter & Gamble Company of Cincinnati, Ohio), are each mixed with one gram samples of substances as set forth in Table I of Example III, supra, until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example III, supra.

EXAMPLE VII

Preparation of Solid Detergent Compositions

Detergents are prepared using the following ingredients according to Example I of Canadian Pat. No. 1,007,948 (incorporated herein by reference):

| Ingredient | Percent By Weight |
|---|---|
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

The detergent is a phosphate-free detergent. Samples of 100 grams each of this detergent are admixed with 0.10, 0.15, 0.20 and 0.25 grams of each of the substances as set forth in Table I of Example III, supra. Each of the detergent samples has an excellent aroma as indicated in Table I of Example III, supra.

EXAMPLE VIII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   57% $C_{20-22}$ HAPS
   22% isopropyl alcohol 20% antistatic agent
1% of one of the substances as set forth in Table I of Example III, supra.

Fabric softening compositions prepared according to Example I at column 15 of U.S. Pat. No. 3,632,396 having aroma characteristics as set forth in Table I of Example III, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example III, supra, is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table I of Example III, supra.

EXAMPLE IX

Hair Spray Formulations

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 Grams of the polymer is dissolved in the alcohol. The following ingredients are added to the PVP/VA alcoholic solution:

| Ingredients | Weight Percent |
|---|---|
| Dioctyl substrate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table I of Example III, Supra. | 0.10 |

The perfume substances as set forth in Table I of Example III, supra, add aroma characteristics as set forth in Table I of Example III, supra, which are rather intense and aesthetically pleasing to the users of the soft-feel, good-hold pump hair sprays.

EXAMPLE X

Conditioning Shampoos

Monoamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

Gafquat ®755N polymer (manufactured by GAF Corporation of 140 West 51st Street, New York, N.Y. (5.0 weight percent) is admixed with 0.1 weight percent sodium sulfite and 1.4 weight percent polyethylene glycol 6000 distearate produced by Armak Corporation. This material is "COMPOSITION B".

The resulting "COMPOSITION A" and "COMPOSITION B" are then mixed in a 50:50 wt ratio of A:B and cooled to 45° C. and 0.3 wt percent of perfuming substance as set forth in Table I of Example III, supra, is added to the mixture. The resulting mixture is cooled to 40° C. and blending is carried out for an additional one hour in each case. At the end of this blending period, the resulting material has a pleasant fragrance as indicated in Table I of Example III, supra.

EXAMPLE XI

Each of the fragrance materials of Table I of Example III, supra, are added to a 50:50 weight:weight mixture of low density polyethylene:polyepsilon caprolactone PCL-700 forming pellets with scents as set forth in Table I of Example III, supra.

Using the apparatus of U.S. Pat. No. 3,505,432 issued on Apr. 7, 1970 (the specification of which is incorporated herein by reference), 75 Pounds of a 50:50 mixture of PCL-700 polyepsilon caprolactone (manufactured by the Union Carbide Corporation of New York, N.Y. having a melting point of about 180°-190° F.): Low density polyethylene, are heated to about 250° F. 25 Pounds of each of the fragrance materials as set forth in Table I of Example III, supra, is then quickly added to the liquified polymer mixture. The temperature is then rasied to about 250° F. and the mixing is effected for 5-15 minutes. The molten polymer enriched with perfume ingredient is then formed into polymer beads or pellets having pronounced scents as described in Table I of Example III. Analysis demonstrates that the pellets contain about 25% of the perfume material so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table I of Example III, supra. The sheets of films are cut into strips of 0.25" in width×3" in length and placed into room air fresheners.

On operation of the room air freshener, after four minutes, the room in each case has an aesthetically pleasing aroma with no foul odor being present, the aroma being described in Table I of Example III, supra.

What is claimed is:

1. The compound having the structure:

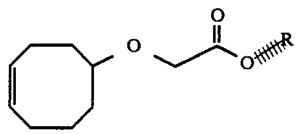

wherein R represents hydrogen, allyl or alkali metal and where the bond:

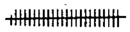

represents an ionic bond or a covalent bond with the proviso that the bond:

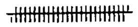

is an ionic bond when R is alkali metal and the bond:
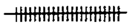
is a covalent bond when R represents hydrogen or allyl.
2. The compound of claim 1 wherein R is allyl and the structure is:
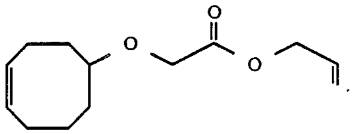
* * * * *